(12) United States Patent
Gershowitz

(10) Patent No.: US 6,918,888 B2
(45) Date of Patent: Jul. 19, 2005

(54) RETROGRADE CANNULA HAVING MANUALLY RETRACTABLE SEALING MEMBER

(75) Inventor: Arthur D. Gershowitz, Ann Arbor, MI (US)

(73) Assignee: Terumo Cardiovascular Systems, Ann Arbor, MI (US)

( * ) Notice: Subject to any disclaimer, the term of this patent is extended or adjusted under 35 U.S.C. 154(b) by 0 days.

(21) Appl. No.: 10/826,250

(22) Filed: Apr. 19, 2004

(65) Prior Publication Data

US 2004/0199111 A1 Oct. 7, 2004

Related U.S. Application Data

(63) Continuation of application No. 10/082,074, filed on Feb. 26, 2002, now abandoned.

(51) Int. Cl.⁷ .............................................. A61M 29/00
(52) U.S. Cl. ...................................................... 604/107
(58) Field of Search ............................ 604/96.01–109, 604/158, 164.01–164.05, 164.08, 164.09, 164.1, 165.02, 171, 264, 912, 915, 916, 920, 191–194

(56) References Cited

U.S. PATENT DOCUMENTS

| | | | | | |
|---|---|---|---|---|---|
| 3,397,699 | A | * | 8/1968 | Kohl | 604/105 |
| 3,634,924 | A | * | 1/1972 | Blake et al. | 29/447 |
| 5,443,449 | A | * | 8/1995 | Buelna | 604/105 |
| 6,102,891 | A | * | 8/2000 | Maria van Erp | 604/99.04 |

* cited by examiner

Primary Examiner—Nicholas D. Lucchesi

(57) ABSTRACT

A retrograde cannula includes coaxial inner and outer bodies, wherein a least of the portion of the inner body is axially slidable within the outer body. The inner body forms an infusion lumen for conducting CPG. A sealing member is mounted adjacent a distal end of the outer body and is expandable into sealing relationship with a wall of a patient's heart. The sealing member includes proximal and distal ends that are moved away from one another to collapse the sealing member in response to axial sliding of the inner body within the outer body to reduce a profile of the cannula, and thereby facilitate movement of the cannula through a patient's body.

2 Claims, 4 Drawing Sheets

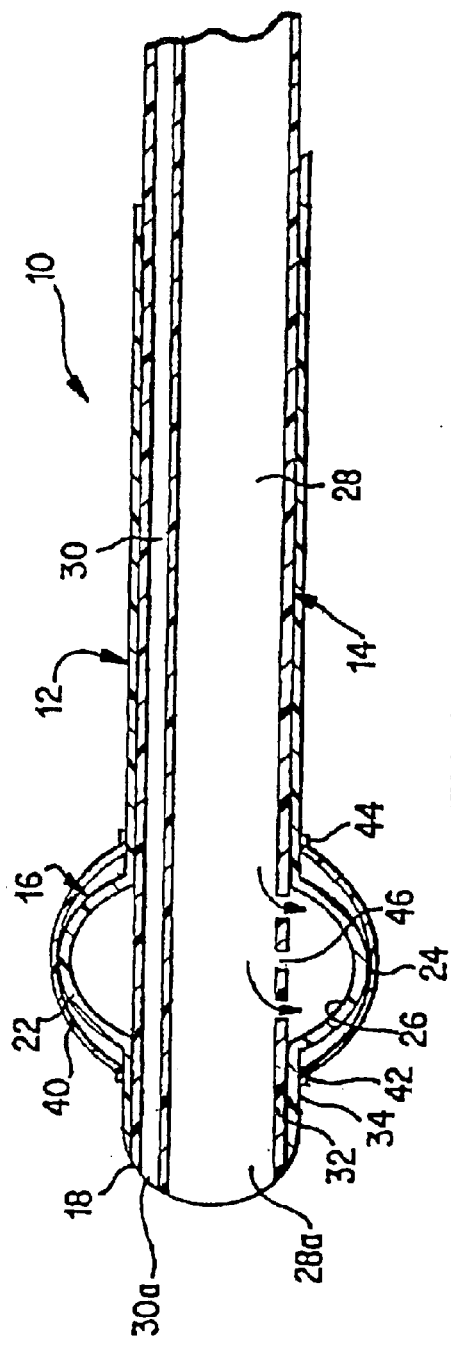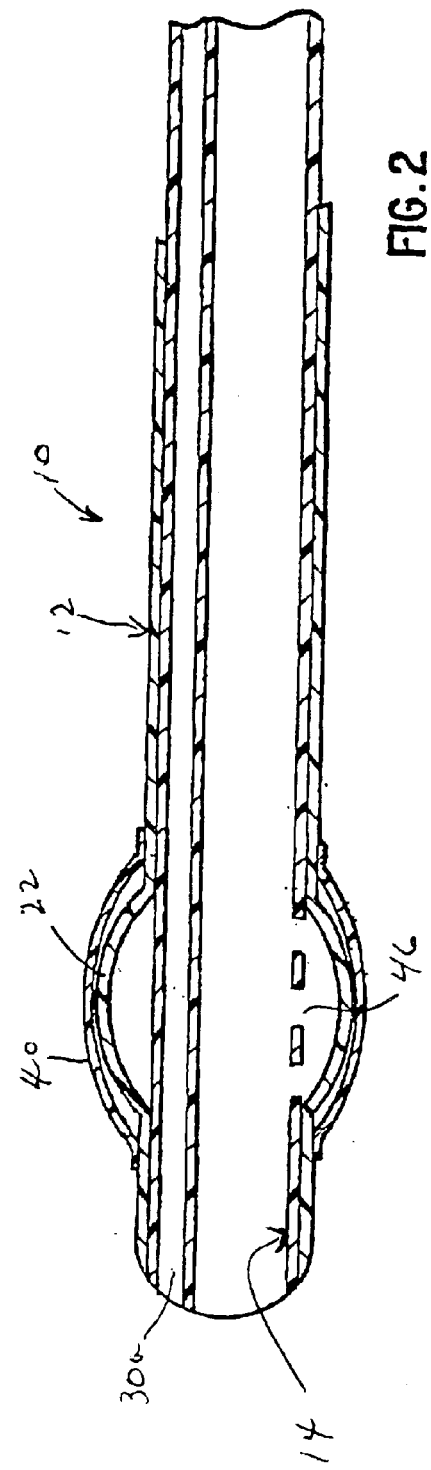

RETROGRADE CANNULA HAVING MANUALLY RETRACTABLE SEALING MEMBER

This application is a continuation of patent application Ser. No. 10/082,074 filed on Feb. 26, 2002, now abandoned.

BACKGROUND OF THE INVENTION

The present invention relates to retrograde cannulas, and in particular to retrograde cannulas used in the delivery of cardioplegia and having automatically expandable sealing members.

Retrograde cannulas are commonly employed during certain cardiac surgical procedures, in order to deliver cardioplegia into coronary veins to effect cardiac arrest by depolarizing cell membranes.

In order to occlude the coronary sinus, the distal end of the cannula includes a sealing member such as an expandible balloon adapted to seal against a wall of the coronary sinus. Balloons may be of the manual-inflating or auto-inflating type. In the auto-inflating type (also referred to as self-inflating), the balloon is in fluid communication with the CPG being delivered to the blood stream and is inflated thereby.

In manual-inflating cannulas, fluid for inflating the balloon is added or withdrawn by means of a syringe. When the balloon of a manual-inflating cannula is deflated, it is common for the balloon to retract snugly against the cannula body when not inflated, whereby the cannula has a reduced profile to facilitate insertion and removal into the body.

In contrast, auto-inflate retrograde catheters typically include a balloon having a relatively permanent shape which varies little between the inflated and deflated states. The inflation of the balloon mainly serves to make the balloon more rigid or turgid, i.e., more less pliant. Thus, the profile of the cannula is not appreciably reduced when the balloon is deflated. This can lead to problems when attempting to insert the cannula into a patient's vessel.

It has previously been proposed in U.S. Pat. No. 5,197,952 to stretch a cannula prior to insertion thereof into a patient. That involves the fixing of a plug within the infusion lumen in the area of the balloon. The plug forms a barrier against which a stylet can be pushed in order to stretch the cannula. The balloon is provided with a fluid inlet disposed proximally of the plug and a fluid outlet disposed distally of the plug, in order to enable fluid (e.g., CPG) to flow through the balloon (and around the plug) after the cannula has been installed. It will be appreciated that the need to install a plug complicates the manufacture and use of the cannula.

It would be desirable to provide an auto-inflate cannula with the ability to significantly reduce its profile and thereby facilitate insertion and removal of the cannula. It would be advantageous to accomplish this without the need to provide a barrier within the cannula body and/or without having to provide an appreciable restriction to the flow of infusion liquid.

SUMMARY OF THE INVENTION

The present invention relates to a retrograde cannula for delivering fluid to a patient's vessel. The cannula comprises a body arrangement which defines a longitudinal axis. The body arrangement includes coaxial inner and outer bodies. At least a portion of the inner body is axially slidable within the outer body. The inner body forms an infusion lumen extending between proximal and distal ends of the inner body for conducting fluid. The infusion lumen includes an outlet adjacent the distal end of the inner body for discharging the fluid. The cannula also includes a sealing member disposed on the body arrangement adjacent a distal end of the outer body. The sealing member is expandable into sealing relationship with the vessel. The sealing member includes proximal and distal ends that are moved away from one other to collapse the sealing member in response to axial sliding of the inner body within the outer body to reduce a profile of the cannula.

The present invention also relates to a method of inserting the retrograde cannula into a vessel of a patient's body. The method comprises the steps of:

A) axially sliding the inner body within the outer body in a first direction to move the proximal and distal ends of the sealing member in opposite directions for collapsing the sealing member to a smaller profile;

B) inserting the reduced-profile cannula into the vessel; and

C) axially sliding the inner body within the outer body in a second direction to move the proximal and distal ends of the sealing member toward one another for permitting the sealing member to extend outwardly.

BRIEF DESCRIPTION OF THE DRAWINGS

The objects and advantages of the invention will become apparent from the following detailed description of preferred embodiments thereof in connection with the accompanying drawings in which like numerals designate like elements and in which:

FIG. 1 is a longitudinal sectional view taken through a cannula according to a first embodiment of the invention, with a sealing element thereof in a non-collapsed state.

FIG. 2 is a view similar to FIG. 1 with the sealing member in a collapsed state.

DETAILED DESCRIPTION OF PREFERRED EMBODIMENTS OF THE INVENTION

Figure 3:
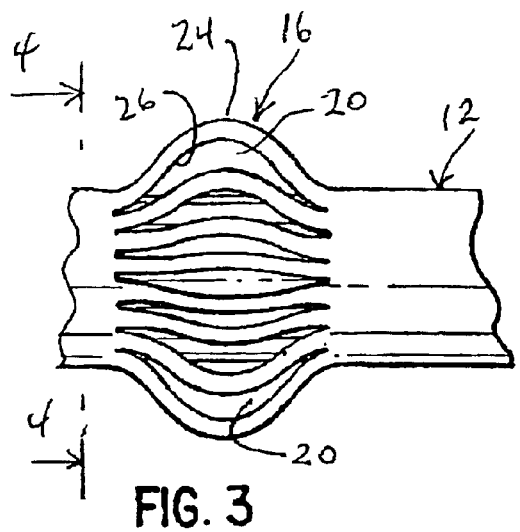
FIG. 3 is a fragmentary side elevational view of a portion of the cannula depicted in FIG. 1, with the sealing element removed.
Figure 4:
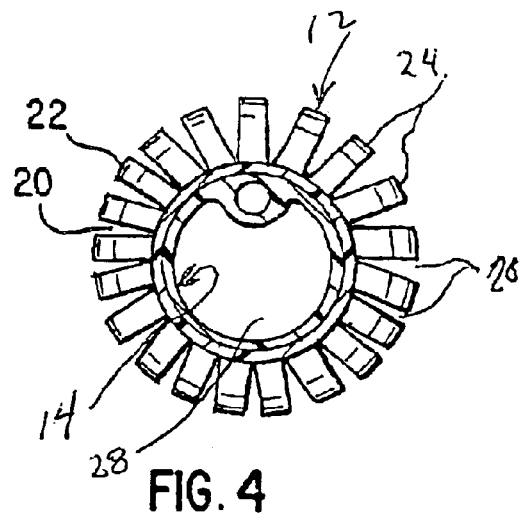
FIG. 4 is a sectional view taken along the line 4—4 in FIG. 3.

Depicted in FIGS. 1–5 is a first preferred embodiment of an auto-inflate retrograde cannula 10 according to the present invention. The cannula 10 comprises an outer body 12 and a coaxial inner body 14. The outer and inner bodies are formed of a plastic material suitable for insertion into a human body, such as PVC, urethane, or silicone for example. The outer body 12 is of cylindrical configuration except for a ribbed portion 16 disposed adjacent a distal end 18 of the outer body. The ribbed portion is of generally bulbous shape and includes slits 20 of any suitable number extending generally in the longitudinal direction of the cannula (see FIG. 3). The slits 20 cause longitudinal ribs 22 to be formed in the ribbed portion that are separated from one another by the slits 20. Each rib 22 is supported solely at longitudinally spaced ends thereof and is of curved shape such that the outer surface 24 thereof is convex, and the inner surface 26 is concave.

The inner body 14 is of cylindrical shape and includes an infusion lumen 28 and a pressure monitoring lumen 30 adjacent thereto. The infusion lumen 28 serves to conduct fluid to the patient's vessel, e.g. to conduct cardioplegia to the heart, and the pressure monitoring lumen 30 enables pressure to be monitored at the distal end of the cannula. Thus, the proximal end of the cannula can be connected to a conventional pressure indicating device (not shown).

The lumens 28, 30 extend from the distal end to the proximal end of the cannula and are open at their distal ends 28a, 30a.

A distal portion 32 of the inner body 14 is affixed to a distal portion 34 of the outer portion, which distal portions 32, 34 are defined as being disposed distally of the ribbed portion 16. The rest of the inner body 14 is slidable relative to the outer body. Thus, by sliding the inner body 14 forwardly while holding the outer body 12 stationary, the ribs 22 can be collapsed, or flattened out, as shown in FIG. 2, to reduce the profile (i.e., to reduce the maximum cross-sectional size) of the cannula.

Affixed to the outer body is an expandable sealing member 40 in the form of a balloon which encompasses the ribbed portion 16. The balloon 40 includes distal and proximal edges 42, 44 affixed to the outer body 12 adjacent respective sides of the ribbed portion 16.

The inner body 14 includes inflation holes 46 which communicate the infusion lumen 28 with the balloon interior. Thus, when fluid, such as cardioplegia, is conducted through the infusion lumen 28 and discharged through one or more outlets at the distal end 28a, the fluid also inflates the balloon, whereby the balloon is inflated, i.e., becomes turgid.

In operation of the FIGS. 1–5 embodiment, the cannula is inserted into the body in the low-profile shape shown in FIG. 2, i.e., with the inner body 14 having been slid forwardly relative to the outer body 12 to collapse, i.e., generally flatten, the ribs 22 and the balloon 40 to a smaller profile. The term "collapse" as used herein does not require a complete collapsing of the ribs, and the balloon, but rather is intended to be broad enough to include a partial collapse. Once the cannula has been inserted into a vessel of the body, e.g. the coronary sinus, the inner body 14 is slid rearwardly, whereby the ribs 22 assume the enlarged profile state of FIG. 1. Preferably in this state, the ribs are able to bear against a wall of the coronary sinus with the non-inflated balloon sandwiched therebetween.

When fluid, such as cardioplegia, is delivered through the infusion lumen 28, the cardioplegia flows through the inflation holes 46 to inflate and stiffen the balloon 40 against the wall of the coronary sinus to seal off any areas not previously sealed. The cardioplegia is thus able to enter the heart vessel.

After an initial charge of cardioplegia has been delivered the flow is halted. Thereupon, the balloon becomes deflated, but the distal end of the cannula remains deployed in the coronary sinus, because the ribs 22 continue to be pressured against a wall of the coronary sinus. Thus, when a subsequent charge of cardioplegia is delivered through the infusion lumen, the distal end of the catheter is still deployed in a desired position.

To remove the cannula from the body, the inner body 14 is slid forwardly to deform (flatten) the ribs 22 and the balloon for reducing the profile of the cannula.

Figure 5:
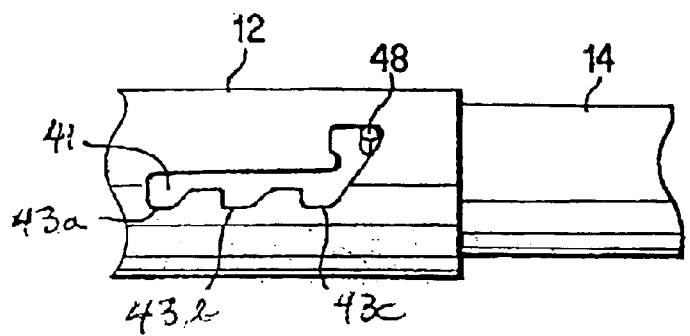
FIG. 5 is a fragmentary view of a proximal portion of the cannula depicting a mechanism for holding inner and outer bodies of the cannula in selected positions.

It may be desirable to provide means for holding the inner body 14 in its various longitudinal positions, which can be done in any of numerous ways. For example, as shown in FIG. 5, the outer body 12 can be provided with a slot 41 having a plurality of notches 43a, 43b, 43c, the number of notches corresponding to respective positions of the inner body 14 relative to the outer body 12, as desired.

The inner body 14 includes a pin 48 received in the slot. Once the inner body 14 is moved axially to a desired position, it can be rotated to position the pin in a respective notch to retain the inner body in position.

Figure 6:
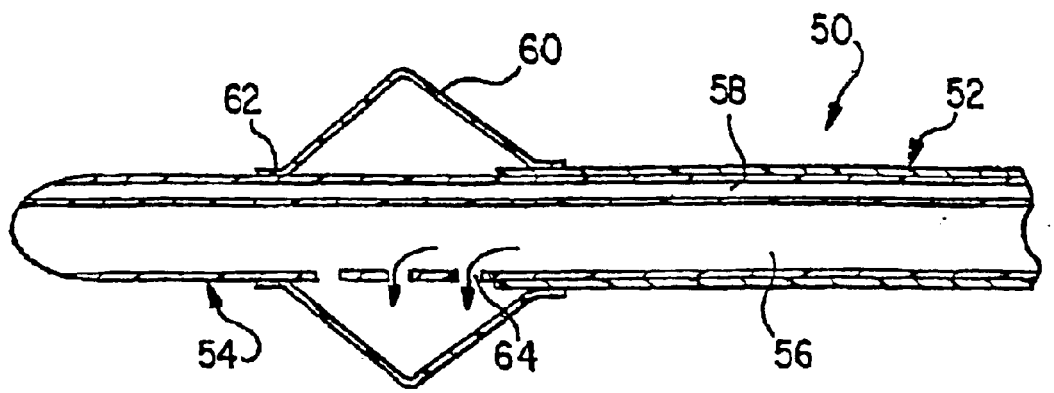
FIG. 6 is a longitudinal sectional view taken through a cannula according to a second embodiment of the invention, with a sealing element thereof in a non-collapsed state.
Figure 7:
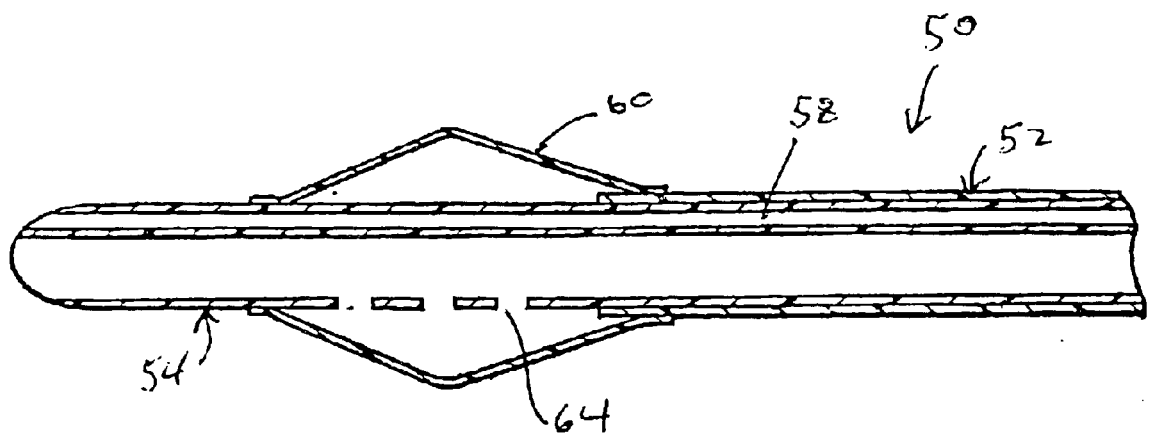
FIG. 7 is a view similar to FIG. 6 with the sealing member in a collapsed state.

Another embodiment of the invention is depicted in FIGS. 6 and 7. In that embodiment, a cannula 50 includes outer and inner bodies 52, 54, with the entire inner body being slidable longitudinally relative to the outer body, i.e., no part of the inner body 54 is fixed to the outer body 52. The inner body 54 includes an infusion lumen 56 and a pressure lumen 58. A balloon 60 has a distal end 62 attached to the inner body 54 and a proximal end 64 attached to the outer body 52. Inflation holes 64 are formed in the inner body 54 to communicate the infusion lumen 56 with the interior of the balloon 60.

Similarly to the earlier-described embodiment, the balloon 60 can be flattened to reduce the profile of the cannula by sliding the inner body 54 forwardly relative to the outer body 52, as shown in FIG. 7.

The cannula 50 is inserted and removed relative to a patient's body with the inner body 54 slid forwardly relative to the outer body 52, i.e., with the cannula in a reduced-profile state (see FIG. 7). Cardioplegia is delivered after the distal end of the cannula has been inserted into the coronary sinus and the inner body 54 has been slid rearwardly. Thus, the balloon 60 is able to be inflated into firm contact with the wall of the coronary sinus by the cardioplegia being delivered.

It will be appreciated that the embodiment according to FIGS. 6 and 7 enables the profile of the cannula to be reduced, like the embodiment according to FIGS. 1–4. If desired, a pin-and-slot arrangement 41, 48 similar to that of FIG. 5 can be employed in order to retain the inner and outer bodies 54, 52 in their relative longitudinal positions.

Figure 8:
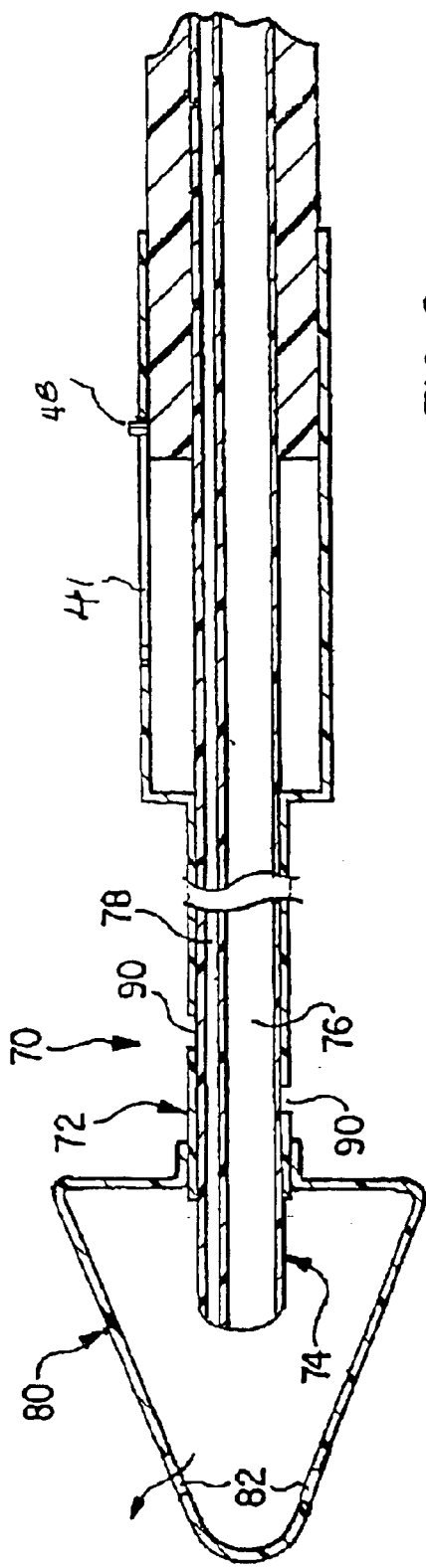
FIG. 8 is a longitudinal sectional view taken through a cannula according to a third embodiment of the invention, with a sealing element thereof in a non-collapsed state.
Figure 9:
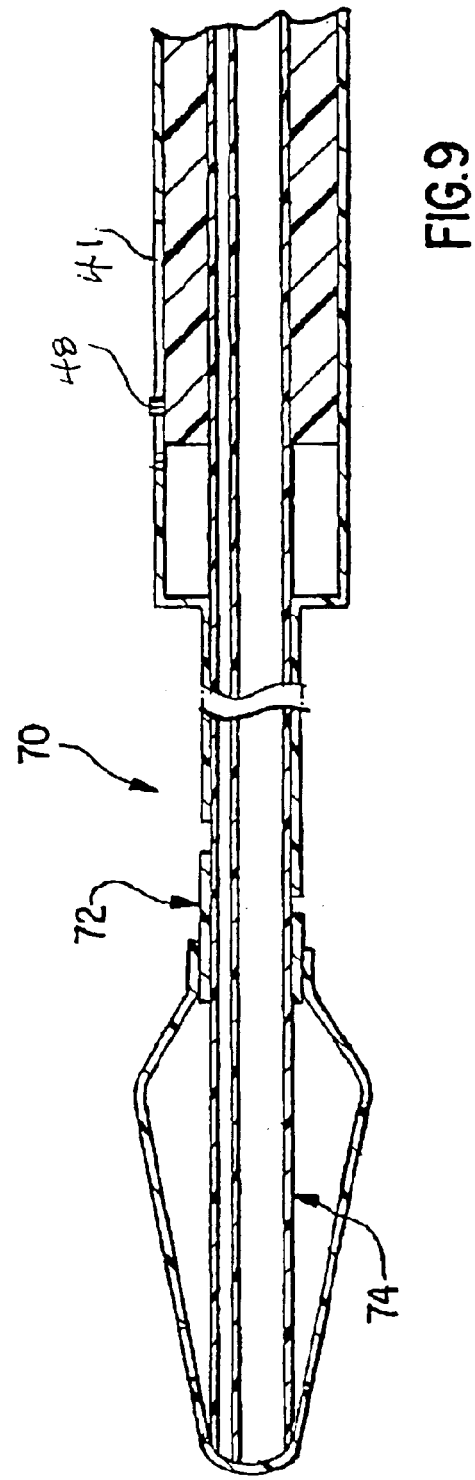
FIG. 9 is a view similar to FIG. 8 with the sealing member in a collapsed state.

A third embodiment of the invention is depicted in FIGS. 8 and 9. Depicted therein is a cannula 70 having outer and inner bodies 72, 74. The inner body 74 is longitudinally slidable relative to the outer body 72, and no part of the inner body 74 is fixed to the outer body. The inner body 74 includes a infusion lumen 76 and a pressure lumen 78. Attached to a distal end of the outer body 72 is the proximal end of a flexible (preferably elastic) expandable sealing member 80 which is not in the form of an inflatable balloon, but rather has a permanent relaxed (normal) shape shown in FIG. 8. The sealing member includes holes 82 adjacent a distal end for discharging cardioplegia, as will be explained. When inserting or removing the cannula 70 relative to a patient's body, the profile of the cannula is reduced by longitudinally extending the inner body 74 forwardly relative to the outer body 72 and into contact with the sealing member 80 to longitudinally extend and collapse the sealing member 80 as shown in FIG. 9. During installation into the patient's body, once the sealing member has reached the desired location in the coronary sinus, the inner body 74 is retracted (i.e., moved to the right in FIGS. 8–9), to return the sealing member 80 to its normal (i.e., expanded) shape and into sealing relationship with the wall of the coronary sinus. Cardioplegia can then be conducted through the infusion lumen 76 and into the sealing member. The cardioplegia exits the sealing member through the holes 82 formed in the sealing member.

It will be appreciated that due to the presence of the holes 82 in the sealing member, the pressurized cardioplegia does not function to inflate the sealing member 80. Rather, the sealing member 80 remains in expanded sealing relationship with the wall of the coronary sinus whenever the inner body 74 is retracted away from the sealing member.

Advantageously, it is possibly to administer an antegrade cardioplegia through an antegrade cannula (not shown) with the sealing member 80 of the retrograde cannula disposed in sealing relationship with the wall of the coronary sinus. In that regard, the outer body 72 is provided with holes 90 that are normally blocked by the inner body 74. However, by retracting the inner body (i.e., to the right in FIGS. 8–9) sufficiently for to expose the holes 90, wherein the distal end of the inner body travels to the right of the holes 90, the holes will be exposed, so that the antegrade cardioplegia can flow through the retrograde cannula from left-to-right by entering the sealing member 80 via its holes 82, and then flowing through the outer body 72 and finally exiting through the holes 90.

It will be appreciated that the present invention provides a retrograde cannula whose profile can be appreciably reduced in order to facilitate the insertion and removal of the cannula, without having to install a plug within the infusion lumen.

Although the present invention has been described in connection with a preferred embodiments thereof, it will be appreciated by those skilled in the art that additions, deletions, modifications, and substitutions not specifically described may be made without departing from the spirit and scope of the invention as defined in the appended claims.

What is claimed is:

1. A retrograde cannula for delivering fluid to a patient's vessel, the cannula comprising:

a body arrangement defining a longitudinal axis and including coaxial inner and outer bodies, the entire inner body and the entire outer body being axially slidable relative to one another, the inner body forming an infusion lumen extending between proximal and distal ends of the inner body for conducting fluid, the infusion lumen including at least one outlet adjacent the distal end of the inner body thereof for discharging the fluid; and a sealing member disposed on the body arrangement adjacent a distal end of the outer body and being expandable into sealing relationship with the vessel, the sealing member including proximal and distal ends that are moved away from another to collapse the sealing member in response to relative axial sliding between the inner and outer bodies in one direction to reduce a profile of the cannula;

wherein the proximal end of the sealing member is affixed to the outer body, and the distal end of the sealing member is affixed to the inner body.

2. The cannula according to claim 1, wherein the sealing member comprises an inflatable balloon, the inner body including communication passages for communicating the infusion lumen with the interior of the balloon.

* * * * *